United States Patent [19]
Nor

[11] Patent Number: 5,389,061
[45] Date of Patent: Feb. 14, 1995

[54] HOCKWRAP

[76] Inventor: Fabio Nor, 603 N. Elm Dr., Beverly Hills, Calif. 90210

[21] Appl. No.: 68,657

[22] Filed: May 27, 1993

[51] Int. Cl.⁶ .............................................. A61N 1/00
[52] U.S. Cl. ........................................ 600/15; 54/82
[58] Field of Search ...................................... 600/9–15; 54/82; 119/143, 29, 96

[56] References Cited

U.S. PATENT DOCUMENTS

| | | |
|---|---|---|
| 2,959,832 | 11/1960 | Baermann . |
| 3,483,494 | 12/1969 | Cromie . |
| 3,546,643 | 12/1970 | Virostek . |
| 3,921,620 | 11/1975 | Nakayama ............................ 600/15 |
| 3,943,912 | 3/1976 | Nakayama ............................ 600/15 |
| 4,022,189 | 5/1977 | Boxer . |
| 4,162,672 | 7/1979 | Yazaki . |
| 4,342,185 | 8/1982 | Pellew .................................. 54/82 |
| 4,456,001 | 6/1984 | Pescatore ............................. 600/14 |
| 4,489,711 | 12/1984 | Latzke . |
| 4,549,532 | 10/1985 | Baermann . |
| 4,587,956 | 5/1986 | Griffin et al. ........................ 600/15 |

FOREIGN PATENT DOCUMENTS

| | | | |
|---|---|---|---|
| 3205048 | 8/1983 | Germany ............................... 600/15 |
| 3530232 | 2/1987 | Germany ............................... 600/15 |
| 894095 | 4/1962 | United Kingdom . |

OTHER PUBLICATIONS

Stratznigg, Dr. Andrea; "Report to the Federal Ministry of Science and Research about the Study of Magnetic Fields"; Ludwig Boltzmann Institute.
Zajc, Dr. Johannes; "Intermediate Report Magnetic Foils–Study on Scars"; I. University Clinic for Dermatology.
Holle, Dr. Jurgen; Brief Report on the Application of "Energy-Pak" Magnetic Foils to prevent Hypertrophic Scar Reactions in the Field of Plastic Surgery.
Wolf, Dr. Walter; Brief Report about the Application of "Energy-Pak" alternating-pole Magnetic Fields for the Improvement and Assistance inthe Ulcus Treatment; Hospital Rudolfstiftung of the City of Vienna.
Kokoschinegg, Dr. P; "The Application of Alternating Magnetic Fields in Medicine".
Pabst, Dr. H. and Kleine, Dr. M. W.; "Testing Static Magnetic Fields for the Therapy of Experimental Hematoma".
Schmid, Dr. A; "The Use of Alternate-Magnetic Foil for Different Pain Conditions of the Locomotor System–An Evaluation of its Effectiveness by Means of Thermography".
Kletter, Dr. G.; "The Use of Alternate-Magnetic Foils in the Treatment of Chronic Lumbago".
Kletter, Dr. G.; "Conservative Therapy of the Cervical Syndromes with Alternate-Magnetic Foils".

*Primary Examiner*—William E. Kamm
*Assistant Examiner*—J. P. Lacyk
*Attorney, Agent, or Firm*—Blakely, Sokoloff, Taylor & Zafman

[57] ABSTRACT

An apparatus for treating subacute and chronic conditions of a hock of an animal. The apparatus comprises a wrap comprising two padded sheets affixed together, a plurality of magnets inserted between the padded sheets to be positioned substantially opposite corresponding accupoints when the wrap is in a wrapped position, means for positioning the apparatus to the hock of the animal, and means for fastening the wrap to the hock of the animal.

10 Claims, 1 Drawing Sheet

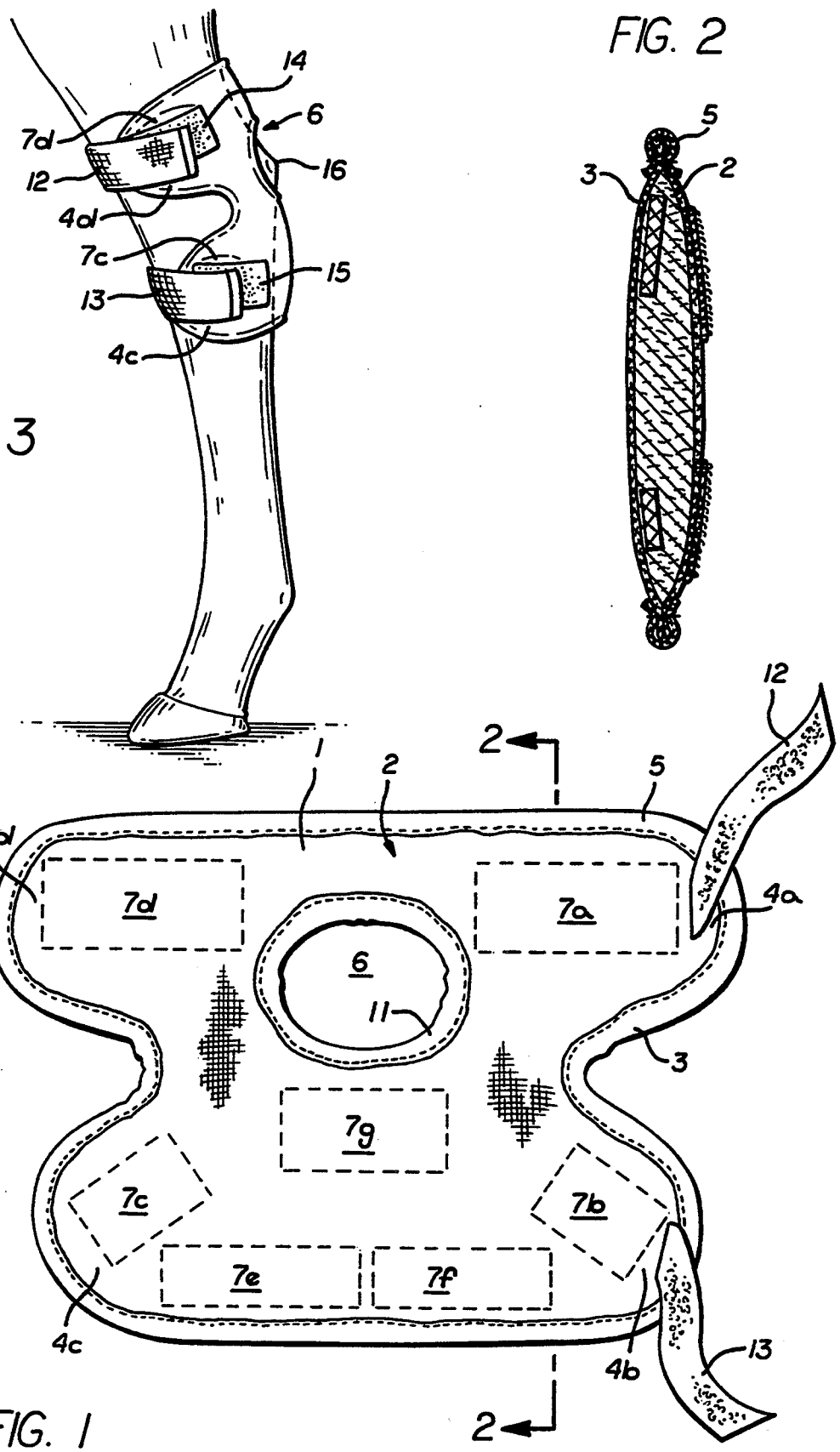

HOCKWRAP

BACKGROUND OF THE INVENTION

1. Field of the Invention

The present invention relates to an apparatus for treating horses, or any other animal, through magnetic field therapy, and more particularly is directed toward an apparatus used to treat subacute or chronic conditions of the hock where blood flow and / or pain relief is required.

2. Background

Thoroughbred horse racing has continued to be a popular and lucrative business over the past century. Although all successful thoroughbreds must have speed and power, they must also be consistently free from injury and soreness. It is apparent that thoroughbred horse owners have little control over the speed of the horse, except with respect to the conditioning of the horse and strengthening of its hocks, a main source of a horse's speed and power. However, such owners do have complete power in maintaining the horse in an injury-free condition especially with respect to its hocks. Therefore, it is vital to keep its hocks free from injury in order for the horse to be able to perform at its optimum level in races or even in everyday activities.

As a result, trainers as well as horse owners have begun using magnetic field therapy to keep the horse's hocks healthy and to aid in the healing process when injured. Magnetic field therapy is recognized by the medical profession as a treatment useful in influencing certain biological processes. For example, magnetic fields cause specific body sites to be heated which stimulates blood circulation and improve oxygen consumption of cells in the specific body site.

Prior to the present invention, magnetic field therapy has been accomplished by bandaging several bipolar magnetic pads to the hock area. Magnetic pads, such as those found in either U.S. Pat. No. 4,489,711 to Latzke or U.S. Pat. No. 4,549,532 to Baermann, were first positioned surrounding the hock in area requiring treatment. While holding the magnetic pads in place, a person would wind a bandage, such as adhesive tape or any elastic material, around the hock to secure the magnetic pads thereto. However, such bandaging techniques have several disadvantages.

One disadvantage is that it is extremely difficult for one person to properly bandage a horse's sore hock. As mentioned above, the magnetic pads are initially secured to the hock by holding them in place. Therefore, any abrupt movement by the horse during application of the bandage, which is a distinct likelihood when a person is tightly bandaging the horse's sore hock, would possibly cause the magnetic pads to shift from their designated position. In such case, the horse would not receive proper treatment to alleviate its soreness and injury. Another disadvantage is that winding bandages around the horse's hock is a time consuming process preventing quick treatment of a horse's hock injury. A further disadvantage associated with the old bandaging technique discussed above, is that the bandages may loosen and not stay in place and therefore the bandages are less effective. This may agitate the horse prompting it to remove the bandages completely thereby leaving the hock uncovered and untreated.

SUMMARY OF THE INVENTION

The apparatus is discussed which overcome the disadvantages and limitations associated with prior art hock bandaging techniques used to treat soreness in a horse's hock.

It is an object of the present invention to provide a wrap which fits securely over the hock and is designed to remain in place to ensure proper treatment thereof.

It is also an object of the present invention to provide a wrap which can be easily secured to the hock.

It is a further object of the present invention to provide a wrap having magnetic pads which come in contact with accupoints for treating conditions such as capped hock, bag spavin, bone spavin, arthritic hock and stringhalt.

It is another object of the present invention to provide a wrap which increases blood circulation around the hock area in order to improve healing and reduce pain experienced by the horse.

These and other objects of the present invention are provided in a wrap placed around a hock of an animal which uses magnetic field therapy for treating subacute or chronic conditions through increased blood circulation and/or pain relief. An apparatus for treating subacute and chronic conditions of the hock, comprising a wrap having a plurality of padded sheets secured together, a plurality of magnetic pads inserted between the plurality of padded sheets and positioned to come into contact with certain accupoints when in a wrapped position, means for positioning the wrap to the hock of the animal, and means for fastening the wrap to the hock of the animal.

BRIEF DESCRIPTION OF THE DRAWINGS

The objects of the present invention will be described with respect to the following figures in which FIG. 1 is an illustration of the preferred embodiment of the present invention.

FIG. 2 is a sectional view of the preferred embodiment of the present invention on line 2—2 of FIG. 1.

FIG. 3 is an illustration of the present invention being applied to a hock of a horse.

DETAILED DESCRIPTION OF THE INVENTION

An apparatus is described which is useful in treating subacute or chronic conditions of a hock of a horse through magnetic field therapy. The preferred embodiment of the present invention might best be described as a wrap attached around a horse's hock to increase blood circulation and reduce pain caused from capped hock, bag spavin, bone spavin, arthritis or stringhalt as well as soreness to the hock joint and check ligaments. It should be borne in mind that the present invention need not be limited in use for horses in general, but may find wide application with many other animals.

As previously discussed herein, FIG. 1 illustrates the preferred embodiment of the present invention. The wrap 1 comprises two flexible sheets 2 and 3, preferably made of 100% cotton to reduce irritation, which are shaped in an hour-glass design with four curved corners 4a–4d. The sheets 2 and 3 are aligned and attached together along their perimeter by sewing, gluing or any other fastening technique. As shown in FIG. 2, a padding lining 5 is attached, preferably by stitching, along the perimeter of the sheets 2 and 3 to reduce irritation and increase comfort to the horse during use of the wrap 1. Although the preferred embodiment illustrates a particular wrap, there are many other types of wraps may be used such as a single sheet having pockets or a wrap having inflexible characteristics.

In order to lessen rubbing on the hock joint which can aggravate the hock as well as to enhance couplability of the wrap 1 to the hock, a cut-out 6 is made proximately between the first and fourth corner of the wrap 1. In its preferred embodiment, the cut-out 6 is circular shaped having a diameter approximately equal to three inches in order to allow the hock joint to be inserted therethrough as shown on FIG. 3. Another padded lining 11, similar to the lining along the perimeter of the wrap 1, is also attached along the perimeter of the cut-out 6. While the shape and size of the cut-out has already been described in detail, such cut-out 6 should not be construed to be limited to any shape or diameter.

As further shown in FIG. 1, a plurality, of magnetic pads 7 are inserted between the sheets 2 and 3 and are positioned to come into contact with certain accupoints proximate to the hock when in a wrapped position as illustrated in FIG. 3. In its preferred embodiment, the magnetic pads are bipolar having alternating positive and negative parallel magnetized strips identical to the magnetic plasters claimed in the Latzke patent identified above. However, any magnetic pads capable of providing a magnetic field for medicinal purposes made be used.

FIG. 1 illustrates seven magnetic pads contained within the wrap 1. These magnetic pads are substantially flat but can be designed with a curvature similar to the seventh magnetic pad 7g. The first four magnets 7a-7d are placed proximate to the curved corners 4a-4d respectively. In the wrapped position as shown in FIG. 3, the first and second magnetic pads 7a and 7b (not shown) are positioned to be in contact with accupoints along an outer side portion of the hock. These magnetic pads 7a and 7b are useful in treating capped hock, bag spavin and bone spavin. Moreover, they provide medicinal treatment for hip, stifle and lumbar-sacral pain of the horse's lower back.

The third and fourth magnetic pads 7c and 7d are arranged to be along an inner side portion of the hock when in the wrapped position. These magnetic pads 7c and 7d are useful in treating such conditions as arthritic hock and stringhalt. The fifth and sixth magnetic pads 7e and 7f are positioned between the second and third corners 7b and 7c in order to provide medicinal magnetic treatment for check ligaments while the seventh magnet 7g is placed below the cut-out having a predetermined curvature to lay flush against the lower portion of hock joint 16 as shown in FIG. 3 so as to treat the same.

The wrap 1 is secured to the hock by at least one fastening members 8. In its preferred embodiment, the fastening member 8 comprises two Velcro straps 12 and 13 and two corresponding Velcro receptors 14 and 15. The straps 12 and 13 are preferably stitched to the first sheet 2 of the wrap 1 proximate to the first and second corners 4a and 4b so that the Velcro portion of the straps faces the first sheet 2. The receptors are preferably stitched to the first sheet proximate to the third and fourth corner 4c and 4d. Alternatively, other fastening members besides Velcro (i.e., a strap combined with a clamp, buckle, etc.) may be used to accomplish the same purpose in maintaining the wrap 1 in a wrapped position.

Referring to FIG. 3, the wrap 1 is applied to a leg of the horse around its hock so that the second sheet 3 rests directly against the hock while the cut-out 6 surrounds a hock joint 16. The straps 12 and 13 are then tightly wound around the hock and coupled to corresponding receptors 14 and 15. As a result, the wrap 1 is positioned in the proper location and securely fastened to the hock to ensure proper treatment, to prevent irritation caused by a loose fitting bandage, and further, to prevent the horse from removing the wrap.

Various studies have been conducted by the University of Minnesota and the Alamo Pintado Equine Medical Center which indicate that magnetic therapy of the type provided by the present invention increases blood circulation over conventional bandage wraps by approximately 30% and increases the healing time over the same by as much as 50%.

The wrap described herein may be manufactured by many different methods and with many different materials. Various types of wraps may be provided to accommodate different areas needing magnetic therapy. While the present invention has been described in terms of a preferred embodiment, other embodiments may come to mind to those skilled in the art without departing from the spirit and scope of the present invention. The invention should, therefore, be measured in terms of the claims which follow.

What is claimed is:

1. An apparatus for aiding in the treatment of subacute and chronic conditions of a hock of a hock of an animal, said apparatus comprising:
    a wrap having a substantially hour-glass configuration;
    a plurality of magnetic pads attached to the wrap so as to be positioned substantially opposite corresponding accupoints when in a wrapped position;
    means for positioning of the apparatus on the hock of the animal, said positioning means including a cut out having a diameter of approximately at least three inches in order to allow a hock joint to be inserted therethrough and to prevent slippage of said wrap after fastening to keep said plurality of magnetic pads in proper alignment with said accupoints; and
    means for fastening the wrap to the hock of the horse.

2. An apparatus according to claim 1, wherein the wrap further comprises two flexible sheets shaped in a substantially hour-glass configuration having four curved corners, and said sheets are aligned and attached together along their perimeter.

3. An apparatus according to claim 2, wherein the wrap is made of 100% cotton.

4. An apparatus according to claim 1, wherein said cut-out further includes a padded lining around a perimeter of said cut out.

5. An apparatus according to claim 1, wherein said wrap includes an inner sheet where said plurality of magnetic pads are positioned along an outer and inner side portions of the hock when the wrap is in a wrapped position around the hock.

6. An apparatus according to claim 5, wherein at least one of said plurality of magnetic pads is curved.

7. An apparatus according to claim 1, wherein said fastening means includes at least one strap and one receptor.

8. An apparatus for aiding in the treatment of subacute and chronic conditions of a hock of an animal, said apparatus comprising:

a wrap comprising a plurality of sheets having an hour glass shape perimeter with four curved corners, said sheets are aligned and attachably affixed to each other along said perimeter, said wrap further comprises:

seven magnetic pads inserted between the plurality of sheets so as to be substantially aligned with corresponding accupoints for medicinal purposes such that a first, second, third and fourth magnetic pads are substantially flat and are each positioned within the wrap at corresponding curved corner, a fifth and sixth magnetic pads are substantially flat and positioned between a second and third corner of the wrap, and a seventh magnetic pad positioned below a cut-out and having a slight curvature;

means for positioning the apparatus on the hock of the animal, said positioning means including said cut-out having a diameter of approximately at least three inches in order to allow a hock joint to be inserted therethrough; and means for fastening the wrap of the hock of the animal said fastening means includes two straps and two corresponding receptors, a first strap is fixedly secured to the wrap at the first curved corner and attaches to a first receptor located at the fourth curved corner and said second strap is fixedly secured to the wrap at the second curved corner and attaches to a second receptor located at the third curved corner with said fastening means preventing slipping of said wrap after fastening to keep said magnetic pads in proper alignment with said accupoints.

9. An apparatus according to claim 8, wherein said cut-out further includes a padded lining around a perimeter of said cut out.

10. A method for aiding in the treatment of subacute and chronic conditions of a hock of an animal, said method comprising:

fastening a wrap on the hock area of the animal, said wrap having a cut-out and a plurality of magnetic pads so as to be positioned substantially opposite corresponding accupoints when in a wrapped position; and positioning said wrap such that the hock joint is inserted through said cut out to secure said magnetic pads in opposite alignment with said corresponding accupoints and preventing slipping of said wrap after fastening to keep said magnetic pads in proper alignment with said accupoints.

* * * * *